US008377906B2

(12) United States Patent
Herzberg et al.

(10) Patent No.: US 8,377,906 B2
(45) Date of Patent: *Feb. 19, 2013

(54) COMPOSITIONS AND METHODS FOR PREVENTING OR REDUCING POSTOPERATIVE ILEUS AND GASTRIC STASIS

(75) Inventors: Uri Herzberg, Bridgewater, NJ (US); Jie Jenny Yuan, Branchburg, NJ (US)

(73) Assignee: Ethicon, Inc., Somerville, NJ (US)

( * ) Notice: Subject to any disclaimer, the term of this patent is extended or adjusted under 35 U.S.C. 154(b) by 231 days.

This patent is subject to a terminal disclaimer.

(21) Appl. No.: 12/359,000

(22) Filed: Jan. 23, 2009

(65) Prior Publication Data
US 2009/0130184 A1 May 21, 2009

Related U.S. Application Data

(63) Continuation-in-part of application No. 10/861,632, filed on Jun. 4, 2004, and a continuation of application No. 11/319,909, filed on Dec. 21, 2005, now abandoned.

(51) Int. Cl.
*A61K 31/717* (2006.01)
*A61K 31/715* (2006.01)

(52) U.S. Cl. ............ 514/57; 514/54; 536/57; 536/56

(58) Field of Classification Search .......... 514/57, 514/54; 536/57, 56
See application file for complete search history.

(56) References Cited

U.S. PATENT DOCUMENTS

| | | | |
|---|---|---|---|
| 3,364,200 A | 1/1968 | Ashton et al. | |
| 4,937,254 A | 6/1990 | Sheffield et al. | |
| 5,180,398 A | 1/1993 | Sheffield et al. | |
| 5,565,210 A * | 10/1996 | Rosenthal et al. | 424/426 |
| 5,888,523 A | 3/1999 | Galask et al. | |
| 6,159,955 A | 12/2000 | Asculai et al. | |
| 6,197,822 B1 | 3/2001 | Hammond | |
| 6,231,888 B1 | 5/2001 | Lerner et al. | |
| 6,242,010 B1 | 6/2001 | Hersh | |
| 6,548,501 B2 | 4/2003 | Hakkinen | |
| 6,605,294 B2 | 8/2003 | Sawhney | |
| 6,652,874 B2 | 11/2003 | Ragavan et al. | |
| 6,689,382 B2 | 2/2004 | Berthel et al. | |
| 6,723,314 B2 | 4/2004 | Keith, Jr. et al. | |
| 6,759,413 B2 | 7/2004 | Mangel et al. | |
| 6,974,869 B2 | 12/2005 | DeLucca | |
| 2002/0188005 A1 | 12/2002 | Farrar et al. | |
| 2003/0118651 A1 | 6/2003 | Jampani et al. | |
| 2003/0212050 A1 | 11/2003 | Van Patten | |
| 2004/0001879 A1 | 1/2004 | Guo et al. | |
| 2004/0022837 A1 | 2/2004 | Hsu et al. | |
| 2004/0109894 A1 | 6/2004 | Shefer et al. | |

FOREIGN PATENT DOCUMENTS

| | | |
|---|---|---|
| EP | 0 274 870 | 7/1988 |
| EP | 0 485 111 | 5/1992 |
| EP | 0 896 822 | 2/1999 |
| EP | 1 027 891 | 8/2000 |
| EP | 1 405 646 | 4/2004 |
| EP | 1405646 A2 * | 4/2004 |
| WO | 98/43477 | 10/1998 |
| WO | 02/34240 | 5/2002 |
| WO | 2004/026200 | 4/2004 |
| WO | 2004/112850 | 12/2004 |
| WO | 2005/049101 | 6/2005 |

OTHER PUBLICATIONS

Kasparek et al. (Zentralblatt fur Chirurgie, (Apr. 2003) vol. 128, No. 4, pp. 313-319) (Abstract sent).*
Watkins et al. (Journal of long-term effects of medical implants, (1997) vol. 7, No. 2, pp. 139-154)(Abstract sent).*
Stella, Valentino J, Expert Opinion of Therapeutic Patents, "Prodrugs as therapeutics," 2004 14(3): 277-280.*
Wolff et al. (Burger's Medicinal Chemistry, 5th Ed., vol. 1, pp. 975-977, 1994).*
Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10) (2004) 2394-2404.*
Brennan, T.J. et al "Characterization of a rat model of incisional pain"—Pain 64 (1996); pp. 493-501.
International Search Report dated Nov. 24, 2005 for corresponding application No. PCT/US2005/018694.
Vuori A; Salo M; Viljanto J., Pajulo O Pulkki K; Nevalainen T; "Effects of Post-Operative Pain Treatment Using Non-Steriodal Anti-Inflammatory Angalgesics, Opiods or Epidural Blockade on Systemic and Local Immune Responses in Children" ACTA Anaesthesiollogica Scandinavica, vol. 48, No. 5, Jul. 2004, pp. 738-749, XP008055633.
Chaplan, S.R. et al, "Quantitative assessment of tactile allodynia in the rat paw", Journal of Neuroscience Methods 53 (1994) pp. 55-63.
Fabio A. Kudo, Toshiya Nishibe, Keiko Miyasaki, Toshifumi Murashita, Masayasu Nishibe and Keishu Yasuda, "Use of Bioresorbable Membrane to Prevent Postoperative Small bowel Obstruction in Transabdominal Aortic Aneurysm Surgery", dept. of Cardiovascular Surgery, Hokkaido University School of Medicine, Sappaoro, Japan et al. Surgery Today (2004) 34: pp. 648-651.
Roman P. Korolkiewica, M.D., Ph.D., Marek Ujda, M.D., Jaraslaw Dabkowski, M.D., Jaroslaw Ruczynski, M.Sc., Piotr Rekowski, Ph.D., and Jacek Petrusewicz, Ph.D., "Differential Salutary Effects of Nonselective and Selective COX-2 Inhibitors in Postoperative Ileus in Rats", Journal of Surgical Research 109, pp. 161-169 (2003).
Makoto Kadowaki, Yasunori Nagakura, Kenichi Tokita, Kaori Hanaoka, and Masaaki Tomoi, "Adenosine A1, Receptor Blockade Reverses Experimental Postoperative Ileus in Rat Colon", European Journal of Pharmacology 458 (2003), pp. 197-200.

(Continued)

*Primary Examiner* — Shaojia Anna Jiang
*Assistant Examiner* — Michael C Henry
(74) *Attorney, Agent, or Firm* — Roberts Mlotkowski Safran & Cole, P.C.

(57) ABSTRACT

Disclosed are compositions and methods for preventing or reducing postoperative ileus and gastric stasis. Such compositions comprise a combination of an oxidized regenerated cellulose component and a non-steroidal anti-inflammatory drug (NSAID) which functions as an inhibitor of cyclooxygenase enzyme (Cox) activity. Such methods comprise administering an effective amount of the composition directly to the serosal surfaces of the gastrointestinal and other visceral organs.

25 Claims, 2 Drawing Sheets

OTHER PUBLICATIONS

Benedicte Y. De Winter, Guy E. Boecksxtanens, Joris G. De Man, Tom G. Moreels, Arnold G. Herman, and Paul A. Pelckmans, "Effects of μ- and k-opioid receptors on postoperative ileus in rats", Div. of Gastroenterology and Pharmacology, Faculty of Medicine, University of Antwerp, Universiteitsplein 1, 2610 Antwert, Belgium, et al., European Journal of Pharmacology 339 (1997), pp. 63-67.

N. Shafiq, S. Malhotra and P. Pandhi, "Effect of Cyclooxygenase Inhibitors in Postoperative Ileus: An Experimental Study, "Methods Find Exp Clin Pharmacol 2002, 24(5): pp. 275-278.

Benedicte Y. De Winter, Guy E. Boeckxstanens, Joris G. De Man, Tom G. Moreels, Arnold G. Herman, and Paul A. Pelckmans, "Effect of adrenergic and nitrergic blockade on experimental ileus in rats", Div. of Gastroenterology and Pharmacology, Faculty of Medicine, University of Antwerp, Universiteitsplein 1, 2610 Antwert, Belgium, et al., British Journal of Pharmacology (1997) 120, pp. 464-468.

Brady et al: "Analgesic Effects of Intraventricular Morphine and Enkephalins in Nondependent and Morphine-Dependent Rats"; The J. of Pharmacology & Experimental Therapeutics, Apr. 12, 1982; pp. 190-197; vol. 222, No. 1; ASPET; U.

* cited by examiner

FIG. 1

COMPOSITIONS AND METHODS FOR PREVENTING OR REDUCING POSTOPERATIVE ILEUS AND GASTRIC STASIS

CROSS REFERENCE TO RELATED APPLICATIONS

This application is a continuation-in-part (CIP) of the co-pending U.S. patent application having Ser. No. 10/861,632; filed Jun. 4, 2004, the contents of which are hereby incorporated by reference in their entirety. This application is also a continuation of the co-pending U.S. patent application having Ser. No. 11/319,909; filed Dec. 21, 2005 the contents of which are hereby incorporated by reference in their entirety.

FIELD

The present invention is directed to the prevention or reduction of postoperative ileus and gastric stasis.

BACKGROUND

Ileus is a major complication following abdominal surgery, and especially an abdominal surgery that involves manipulating the intestines and other abdominal organs. Specifically, paralytic ileus is the functional inhibition of peristaltic motility of the intestines. It prevents the absorption of drugs and nutrients, increases patient discomfort and pain, prolongs patient hospitalization and increases postoperative health care costs.

Care of the patient after surgery frequently does little to address the ileus condition and, in fact, often adds complications. Since opiates decrease intestinal motility, analgesic drugs such as morphine and codeine administered after surgery only exacerbate the severity and increase the incidence of postoperative ileus.

The main approaches for treating postoperative ileus and gastric stasis involve the use of systemic drugs. Currently there is only one drug, which has tentative approval for treating the condition. Specifically, a peripherally active opiate antagonist, Entereg (By Adolor and GlaxoSmithKline), has been submitted to the FDA for treating POI. Blocking peripheral opiate receptors is indeed a viable approach in preventing postoperative ileus. (See, for example, US 2002/0188005) Yet, this approach is only valuable in blocking the gastrointestinal effects of opiates which are commonly administered as analgesics following surgery. Such drugs are not likely to have an effect on the intestinal and gastric stasis that is opiates independent. Other approaches involve other mediators such as blocking the adenosine A1 receptor, blocking the Cox2 enzyme, and using the anti-inflammatory cytokine IL-11, etc. Blocking the PAR-2 enzyme has also been suggested as an approach (See, for example, WO 9843477.)

Common to all these approaches is the systemic delivery of an agent that enhances gastric and intestinal motility, or prevents the stasis and ileus of the stomach and intestines. However, systemic drug delivery, while simple, carries with it the side effect profile of the drug. For example, when systemically delivering anti-inflammatory drugs, such as NSAIDs, tissue healing will be affected. Cytokine injections such as IL-11 will affect the immune response of the patient, and systemic administration of A1 antagonists will have effects on the nervous system. Furthermore, for systemic drug delivery, non-target organs will also be affected.

While the pathology mediating the ileus and stasis condition is not clear, animal studies point to the activation of the cyclooxygenase enzymes (Cox1 and Cox2) as being at least partially responsible for this condition. While many Cox1 and Cox2 inhibitors are available, the systemic administration of Cox1 and Cox2 inhibitors to the post operative patient is, as with other systemically delivered agents, undesirable. This is due to their gastrointestinal side effect profile, their inhibitory effects on wound healing and their platelet inhibition.

Given the foregoing considerations, there is a continuing need to identify treatment or prevention methods and products which are suitable and effective for preventing, treating and ameliorating postoperative ileus and gastric statis. Such methods and products are ideally those which directly address the pathology of the condition but do not involve the systemic administration of drugs which can cause undesirable side effects. Accordingly, the present invention provides compositions and methods for preventing or reducing gastric stasis and postoperative ileus, which compositions and methods involve direct administration of therapeutic agents to the serosal surfaces of the affected organs.

SUMMARY

In one embodiment, the present invention is directed to compositions suitable for administration to the serosal surfaces of the gastrointestinal and other visceral organs to prevent or reduce postoperative ileus and gastric stasis. Such compositions comprise an oxidized regenerated cellulose component and a nonsteroidal anti-inflammatory drug (NSAID) which functions as a cyclooxygenase enzyme inhibitor, i.e., an inhibitor of Cox1 and/or Cox2 enzymes.

In another embodiment, the present invention is directed to methods for preventing or reducing postoperative ileus and gastric stasis. Such methods comprise administering directly to the serosal surfaces of the gastrointestinal or other visceral organs an effective amount of a composition which comprises an oxidized regenerated cellulose component and a non-steroidal anti-inflammatory drug (NSAID) which functions as a cyclooxygenase enzyme inhibitor, i.e., an inhibitor of Cox1 and/or Cox2 enzymes.

The present invention makes use of the ability of oxidized regenerated cellulose (ORC) in micronized particles or sheet form to adhere to serosal surfaces of intestines or other organs, together with its ability to locally deliver cyclooxygenase enzyme inhibitors. It is noted that prostanoids molecules are released during the inflammatory process when tissue is irritated in the course of surgery which can subsequently initiate and maintain ileus. By locally releasing a Cox inhibitor at the serosal level, production of prostanoids from the manipulated serosa can be reduced, and gastrointestinal motility can be improved.

DETAILED DESCRIPTION

Oxidized Regenerated Cellulose Component

The present invention is based on the ability of oxidized regenerated cellulose fabrics or micronized oxidized regenerated cellulose (ORC) particles or ORC-containing foams or agglomerates, when allied to the wet serosal layers of the intestines and other visceral organs, to adhere to such surfaces tightly. Accordingly, an essential component of the compositions herein is an appropriate form of oxidized regenerated cellulose which serves as a delivery agent for the active Cox inhibitor(s).

Oxidized regenerated cellulose and a detailed description of its method of manufacture is set forth in U.S. Pat. No. 3,364,200, which discloses the preparation of carboxylic-oxidized cellulose with an oxidizing agent such as dinitrogen tetraoxide in a Freon medium, and U.S. Pat. No. 5,180,398, which discloses the preparation of carboxylic-oxidized cellulose with an oxidizing agent such as nitrogen dioxide in a per-fluorocarbon solvent. Both of these U.S. patents are incorporated herein by reference as if set forth in their entirety. After oxidation by either method, the carboxylic-oxidized cellulose is thoroughly washed with a solvent such as carbon tetrachloride, followed with an aqueous solution of 50 percent isopropyl alcohol (IPA), and finally with 99% IPA.

The oxidized regenerated cellulose that may be used in one embodiment also comprises fabrics utilized as conventional adhesion barriers or conventional hemostatic wound dressings. Such fabrics include Interceed® absorbable adhesion barrier; Surgicel® absorbable hemostat; Surgicel Nu-Knit® absorbable hemostat; and Surgicel® Fibrillar absorbable hemostat; all available from Gynecare Worldwide or Johnson & Johnson Wound Management Worldwide, divisions of Ethicon, Inc., Somerville, N.J., a Johnson & Johnson Company; as well as Oxycel® absorbable cellulose surgical dressing from Becton Dickinson and Company, Morris Plains, N.J. Oxidized cellulose powder such as Curacel® oxidized regenerated cellulose powder from Curaspon Healthcare, the Netherlands, or micronized particles made from Surgicel® Fibrillar absorbable hemostat or Interceed® absorbable adhesion barrier also may be used.

NSAID Cox Inhibitor Component

The compositions and methods herein involve the combination of oxidized regenerated cellulose, in a variety of forms and prepared using a variety of techniques and adjuvants as hereinafter described, with a pharmaceutically active component which functions as an inhibitor of the activity of cyclooxygenase (Cox1 and/or Cox2) enzymes. Such Cox inhibitors, generally in the form of non-steroidal, anti-inflammatory drugs (NSAIDs), are well-known materials.

NSAID Cox Inhibitor Component

The NSAID Cox inhibitors utilized can be those which are either non-selective or selective. Non-selective Cox inhibitors are those which inhibit the activity of both the Cox1 and Cox2 variants of the cyclooxygenase enzyme. Selective Cox inhibitors are those which selectively inhibit the activity of either the Cox1 or Cox2 enzyme forms preferentially.

The NSAID Cox inhibitors useful herein can be selected from the following categories:

(1) the propionic acid derivatives;
(2) the acetic acid derivatives;
(3) the fenamic acid derivatives;
(4) the biphenylcarboxylic acid derivatives;
(5) the oxicams; and
(6) the Cox2 inhibitors.

The Cox inhibitor compounds in groups (1) through (4) typically contain a carboxylic acid function. However, those acids are sometimes administered in the form of their pharmaceutically acceptable acid addition or alkali metal salts, e.g., sodium salts.

The propionic acid derivatives for use as Cox inhibitors herein include, but are not limited to, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Structurally related propionic acid derivatives having similar cyclooxygenase inhibiting properties are also intended to be encompassed by this group. Presently preferred members of the propionic acid group include ibuprofen, naproxen, flurbiprofen, fenoprofen, ketoprofen and fenbufen.

The acetic acid derivatives for use as Cox inhibitors herein include, but are not limited to, indomethacin, sulindac, tolmetin, zomepirac, diclofenac, fenclofenac, alclofenac, ibufenac, isoxepac, furofenac, tiopinac, zidometacin, acemetacin, fentiazac, clidanac and oxpinac. Structurally related acetic acid derivatives having similar cyclooxygenase inhibiting properties are also intended to be encompassed by this group. Presently preferred members of the acetic acid group include zomepirac, diclofenac, indomethacin and sodium salts thereof.

The fenamic acid derivatives for use as Cox inhibitors herein include, but are not limited to, mefenamic acid, meclofenamic acid, flufenamic acid, niflumic acid and tolfenamic acid. Structurally related fenamic acid derivatives having similar cyclooxygenase inhibiting properties are also intended to be encompassed by this group. Presently preferred members of the fenamic acid group include mefenamic acid, meclofenamate acid, and sodium salts thereof.

The biphenylcarboxylic acid derivatives for use as Cox inhibitors herein include, but are not limited to, diflunisal and flufenisal. Structurally related biphenylcarboxylic acid derivatives having similar cyclooxygenase inhibiting properties are also intended to be encompassed by this group. Preferred members of this group are diflunisal and flufenisal.

The oxicams for use as Cox inhibitors herein include, but are not limited to, piroxicam, sudoxicam, isoxicam and CP-14, 304. Structurally related oxicams having similar cyclooxygenase inhibiting properties are also intended to be encompassed by this group. A preferred member of this group is piroxicam.

The selective Cox2 inhibitors for use herein include those selected from the group consisting of Celecoxib, Rofecoxib, valdecoxib, Paracoxib and MK 663. Structurally related NSAIDs having similar Cox2 inhibiting properties are also intended to be encompassed by this group. Preferred members of this group include Celecoxib and Rofecoxib.

Cox inhibitors of all of the foregoing types, as well as other NSAIDs suitable as Cox inhibitors, are described in greater detail in U.S. Pat. Nos. 6,689,382 and 6,231,888, United States Patent Publication No. 2003/0212050 and European Patent Application No. EP-A-485,111. All of these patent documents are incorporated herein by reference.

Especially preferred Cox inhibitors for use in this invention are NSAIDs which are acids having a secondary amine group. Particularly preferred NSAIDs of this type include 2-[(2,6-1dichlorophenyl)amino] benzeneacetic acid (also referred to as diclofenac), or 2-[(2,6-dichlorophenyl)amino]-benzeneacetic acid, monosodium salt, or 2-[(2,3-dimethylphenyl)amino]-benzoic acid (also referred to as mefenamic acid). These particular NSAID Cox inhibitor compounds are effective for preventing postoperative ileus and gastric stasis. Those Cox inhibitors of the foregoing listed categories but which do not contain a secondary amine group may also be used in the invention herein.

It is understood that the present invention contemplates the use of not only the hereinbefore-described NSAID Cox inhibitor compounds themselves, but also their pro-drugs which metabolize to the compounds and the analogs and biologically active salt forms thereof, as well as optical isomers which provide the same pharmaceutical results. Thus for purposes of this invention, the term "non-steroidal anti-inflammatory drug" is meant to include all derivatives or precursors such as salts, esters, pro-drugs, analogs, isomers, etc. which are NSAIDs themselves or which can yield materials which function as NSAIDs.

Composition Preparation Procedures and Preparation Adjuvants

The compositions herein can take a number of different forms depending upon the type and form of oxidized regenerated cellulose used to prepare the composition. Also, it may be appropriate to utilize various types of compositions adjuvants in preparing such compositions in their several forms.

In the embodiment where a fabric or textile of oxidized regenerated cellulose is utilized, a solution of the Cox inhibitor active agents may be incorporated into the composition by (a) dip coating the oxidized regenerated cellulose fabric or textile in a solution or suspension of the Cox inhibitor; (b) spray coating a solution or suspension of the Cox inhibitor onto the oxidized regenerated cellulose fabric or textile; (c) laminating at least one polymeric film formed from an aqueous, non-aqueous or organic solution or suspension of the Cox inhibitor onto the oxidized regenerated cellulose fabric or textile; or (d) forming a microporous polymeric matrix with Cox inhibitor, and oxidized regenerated cellulose powders or textile.

Polymers that may be laminated onto the oxidized regenerated cellulose fabric or textile may be water-soluble polymers that include, but are not limited to, poly(acrylic acid), hydroxylpropyl methyl cellulose, polyvinyl pyrrolidone, polyethylene glycol, and polyethylene oxide. These polymers, used to accurately control the dosage or loading of the Cox inhibitor onto the fabric or textile during processing, are fast dissolving in an aqueous environment.

Polymers that may be used as a binder component or to form the microporous polymeric matrix of Cox inhibitor onto an oxidized regenerated cellulose fabric or textile (as described hereinbefore), include but are not limited to, polysaccharides and proteins. Such polysaccharides include, without limitation, cellulose, alkyl cellulose, e.g. methylcellulose, alkylhydroxyalkyl cellulose, hydroxyalkyl cellulose, cellulose sulfate, salts of carboxymethyl cellulose, carboxymethyl cellulose, carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylose, amylopectin, poly-N-glucosamine, polymannuronic acid, polyglucuronic acid polyguluronic acid, and derivatives of any of the above. Examples of proteins include, but are not limited to, collagen and gelatin.

In addition to fabric or textile forms, the oxidized regenerated cellulose component may be in the form of particles. For example, in one embodiment, oxidized regenerated cellulose textile may be micronized to particles having an average particles size ranging from 1 to 1000 microns, and preferably of 20 to 25 microns, as measured by a Beckman Coulter Particle Size Analyzer [LS13320, Tornado Dry Powder System and Universal Liquid Module]. In this embodiment, the composition comprises oxidized regenerated cellulose particles and Cox inhibitor particles having an average particle size of 1 to 1000 microns, and preferably 1 to 100 microns. For example, the oxidized regenerated cellulose powders may be blended with the Cox inhibitor powders for final use. To achieve a range of oxidized regenerated cellulose particle sizes to be used in a co-blended powder, oxidized regenerated cellulose may be subjected to, for example, cryogenic milling.

In other embodiments, the composition of the present invention may comprise oxidized regenerated cellulose particles; a porous binder component; and a Cox inhibitor, and may be in the form of a foam sponge, foam beads or agglomerates.

In alternate embodiments, oxidized regenerated cellulose particles or short fibers utilized to make foam sponges, foam beads or agglomerates may have an average size ranging from about 10 to about 5000 microns, preferably from about 680 microns to about 4350 microns. Such oxidized regenerated cellulose particles may be made by milling the oxidized regenerated cellulose fabrics described above or any oxidized regenerated cellulose textile with a cutting blade of a motor-driven mill to the desired fiber length using a Thomas-Wiley® Laboratory Mill, Intermediate Model cutting blade. The motor-driven mill, with two stationary blades and a motor with four cutting edges revolving at high speed to produce a shearing action, is ideal for rapid milling of fabric samples. For example, the oxidized regenerated cellulose particles may be made by placing an oxidized regenerated cellulose textile, such as Surgicel® absorbable hemostat; Surgicel Nu-Knit® absorbable hemostat; or Surgicel® Fibrillar absorbable hemostat, or an oxidized regenerated cellulose, in a stainless steel foil pouch filled with liquid nitrogen and submerging the foil pouch in liquid nitrogen. The foil pouch is then passed through a dual wheel roller at, for example, 6 in/min, yielding oxidized regenerated cellulose having an average particle size of 0.035-4.35 mm.

In all of the foregoing embodiments of the compositions herein and in the methods of this invention, the mass ratio of the Cox inhibitor to the oxidized regenerated cellulose (ORC) can generally range from about 1:1000 to about 1:3 More preferably, this mass ratio of Cox inhibitor to ORC will range from about 1:100 to about 1:10. In the compositions herein, the active Cox inhibitor can generally range in concentration from about 0.01% by weight to about 10% by weight, more preferably from about 0.1% by weight to about 3% by weight of the composition.

The compositions may also benefit from having a variety of substances included such as stabilizers, wetting agents, or preservatives. Other drugs may also be added to the composition, so long as it is compatible with the NSAID Cox inhibitor and the remaining ingredients. These drugs include antibiotics, antiviral, and anti-fungal agents. Since tissue sites are occasionally infected, an antibiotic or anti-microbial agent may also be combined with the composition.

When brought into contact with fluids within the abdominal cavity, such as serosal moisture, blood, or peritoneal fluid, the composition of the present invention swells as a result of the hydrophilic nature of the oxidized regenerated cellulose. The composition may also be exposed to an exogenous source of aqueous fluid, preferably sterile phosphate buffered saline, immediately prior to application so as to aid in delivering the composition. Other suitable aqueous solutions that may be used just prior to implantation include sterile forms of Ringers solution, saline, and dextrose solution. In certain of the forms described above, the flowability of the wet composition allows it to conform to irregularities, crevices, cracks, or folds in the serosal tissue site.

Composition Use to Prevent or Reduce Postoperative Ileus and Gastric Stasis

In its method aspect, the present invention comprises administering directly to the serosal surfaces of the gastrointestinal or other visceral organs an effective amount of a composition as hereinbefore described. Such a composition utilizes oxidized regenerated cellulose as a carrier for the NSAID, which functions as a Cox1 and/or Cox2 inhibitor.

As noted, the ORC allies itself to the wet serosal layers of the intestines or other organs and adheres to those surfaces tightly. When attempting to deliver any therapeutic agent such as Cox inhibitors to the manipulated serosa, it is important that the therapeutic agent not "wash away" from the area where it is applied. Hence, a carrier such as ORC is especially efficacious. The ORC carrier does not promote and, in fact, may prevent post surgical adhesions of intestines and other organs.

ORC particles while dry adhere tightly to the serosa, but after the particles are wetted, a thin film remains on the serosa, without causing adhesions of the intestines to each other. Knitted fabric of ORC performs in similar fashion. So in addition to non-systemic delivery of Cox inhibitors to prevent postoperative ileus, such fabrics are also useful in preventing adhesions of intestinal organs and other internal organs following abdominal surgeries.

EXAMPLES

To illustrate the present invention, several types of compositions containing various forms of oxidized regenerated cellulose and diclofenac, a known Cox inhibitor, are prepared. Combinations of oxidized regenerated cellulose and diclofenac, such as are used in the compositions and methods of this invention, are also evaluated via in vivo testing for their ability to alleviate postoperative ileus.

Example 1

Dry Powder Mixtures

Co-blended powders of oxidized regenerated cellulose and diclofenac are prepared by mixing particles of a diclofenac sodium component and particles of oxidized regenerated cellulose. Oxidized regenerated cellulose particles are produced from Surgicel Fibrillar™ absorbable hemostat, which is first frozen in liquid nitrogen and then milled using a cryogenic mill.

The cryogenic milling process used to form ORC particles is described in detail as follows. Approximately 0.5 grams of 2 cm×2 cm squares Surgicel Fibrillar™ are added to a steel cryo-tube. The cryo-tube is a stainless steel centered tube, which incorporates an internal metal impactor and is sealed at each end with stainless steel vial caps. The cryo-tube containing the oxidized regenerated cellulose is placed into the SPEX-6750-115 cryogenic mill, which is a cryogenic impact grinder with a self-contained liquid nitrogen tub and insulated case. When the lid is closed, the charge loader containing the cryo-tube is immersed in liquid nitrogen. A pre-cool time of four minutes is programmed before the cryogenic milling process begins. The cryogenic milling process time is set for three minutes, and the impact rate is set at ten (i.e., two impacts per second). When the mill is activated, the metal agitator moves rapidly due to a fluctuating magnetic field produced by the machine, and the contained material is processed into powder form. The material is collected in a clean glass jar and held under vacuum to remove any residual moisture that may have collected on the powder. The powders are stored under vacuum prior to use. The particle size of the milled material is determined by using a Beckman Coulter Particle Size Analyzer. The average particle size ranged from 20 to 25 microns.

The particles of oxidized regenerated cellulose prepared in this manner are combined with diclofenac sodium powders by dry blending. In preparing such blends, an amount of approximately 20 mg oxidized regenerated cellulose powders and 1 mg diclofenac sodium powder are weighed separately and mixed together in a clean glass vial. This corresponds to a 20:1 oxidized regenerated cellulose powder to diclofenac sodium powder weight ratio. Other weight ratios of oxidized regenerated cellulose powders to diclofenac sodium powders are also made in the range of 40:1 to 2:1. This corresponds to concentrations of NSAID Cox inhibitor in the compositions of from about 2.5% to about 50% by weight.

The blends of diclofenac and oxidized regenerated cellulose powder so prepared are shielded from any light source. Samples of these compositions are stored in glass Wheaton vials, vacuum dried at room temperature for 24 hours, sealed under nitrogen, and packaged in low temperature foil pouches and Cobalt sterilized (25 kGy). Samples are then stored in a cabinet purged with nitrogen gas at room temperature.

Example 2

Diclofenac-Coated Interceed®

Interceed® (IC) fabric samples loaded with diclofenac sodium (DFNa) are prepared using a solution coating method. Several DFNa aqueous solutions are made by adding certain amounts of DFNa into 20 ml deionized water in 25-ml glass vials. The solutions are shaken until all the DFNa particles are dissolved in the water. The following table lists all the solutions that are made:

| Samples ID | Solution concentration (mg/ml) | Total DFNa per sample (mg) |
| --- | --- | --- |
| IC-2.0 mg | 15.0 | 2.0 |
| IC-1.0 mg | 7.5 | 1.0 |
| IC-0.3 mg | 2.25 | 0.3 |
| IC-0.1 mg | 0.75 | 0.1 |

The Interceed® samples are cut into 1 inch by 1 inch squares. A Teflon release film is put in an aluminum pan, and the pan is put on a balance. The balance is zeroed so that the weight of the Teflon film is tared. One or multiple drops of DFNa solution are dropped onto the Teflon film, and weighed to about 133 mg. The pan is taken out of the balance. An Interceed® sample is laid on top of the solution drops, and this lets solution spread over the Interceed®. To make the solution wet the Interceed® uniformly, the Interceed® sample is slightly manipulated so that all the solution is absorbed onto the Interceed® uniformly. The pan with the sample is then put into a vacuum oven, where vacuum drying is carried out for at least 48 hours. The above procedures are repeat so that multiple DFNa coated Interceed® samples are made.

The dried DFNa/Interceed® samples are then packaged into a tyvek envelope, which is then enclosed in a foil pouch under nitrogen. The package is cobalt sterilized at 25 kGy.

When the DFNa-coated Interceed® samples are examined with a Scanning Electron Microscope, the diclofenac crystals are clearly shown on both sides and between the interstices of the Interceed® fibers. Because the total solution absorbed onto the Interceed® is just enough to wet the Interceed®, no curling of the edges is observed. In addition, because no excess of solution is present, the conversion of DFNa to its acid form, diclofenac acid (DFH), occurs on the Interceed® instead of in the solution. Thus, variation in drug loading due to precipitation of DFH in the solution is avoided.

The total drug content for the group IC-2.0 mg samples is measured by High Performance Liquid Chromatography (HPLC) method. The results are shown in Table 1. The results show that the DFNa contents measured by the HPLC analytical method correlate well with those calculated by weight measurement. This suggests that the total drug contents can be easily controlled by the total volume of DFNa solution applied on each Interceed® sample.

TABLE 1

Total Drug Contents on Interceed ® Samples

| Sample ID | Sample Wt (mg) | DFNa Measured HPLC (mg) | DFNa Calculated by Wt (mg) |
|---|---|---|---|
| IC-2.0 mg-1 | 72.58 | 2.03 | 1.99 |
| IC-2.0 mg-2 | 78.16 | 2.05 | 2.02 |
| IC-2.0 mg-3 | 76.07 | 1.98 | 1.97 |
| IC-2.0 mg-4 | 69.75 | 1.95 | 2.00 |
| IC-2.0 mg-5 | 65.36 | 2.05 | 2.01 |
| Average |  | 2.01 | 2.00 |
| STD Dev |  | 0.04 | 0.02 |

Example 3

In Vivo Testing of Ileus Alleviation

To test the efficacy of the compositions and methods of the present invention, an animal model of post operative ileus is used. This model and method of testing used herein is described in De Winter et al., "Effect of adrenergic and nitrergic blockade on experimental ileus in rats," *Br J Pharmacol.* 1997 February; 120(3):464-8 and De Winter et al., Effects of mu- and kappa-opioid receptors on postoperative ileus in rats," *Eur J Pharmacol.* 1997 Nov. 19; 339(1):63-7. These articles are incorporated herein by reference.

In this in vivo testing, male, Sprague Dawley rats, weighing 250-275 g (6-8/group) are fasted for 24 hours and divided into groups which receive different treatment regimens. Each group, and the treatment that group receives, are described as follows. (For Test Groups 4-7 and 9-10 the Interceed®-based compositions described in Example 2 hereinbefore are used.)

DFNa coated Interceed® samples, which are used for Test Groups 4 to 7 and 9 to 10, are prepared by the solution coating method described in Example 2. All the samples are 2 cm by 2.5 cm in size. The sample identifications and the total DFNa contents are listed in Table 2.

TABLE 2

Samples for In Vivo Testing

| Sample ID | DFNa per Sample* (mg) |
|---|---|
| IC-2.0 | 2.00 +/− 0.019 |
| IC-1.0 | 1.01 +/− 0.007 |
| IC-0.3-A | 0.30 +/− 0.003 |
| IC-0.1 | 0.10 +/− 0.001 |
| IC-0.3-B | 0.30 +/− 0.001 |

*The DFNa content per sample is calculated based on the weight measurements.

1. Control Group (labeled as "Anesthesia") is anesthetized with a xylazine/ketamine cocktail, injected intramuscularly (IM).

2. Experimental Group 2 (labeled as "Sx") is anesthetized with a xylazine/ketamine cocktail, injected IM, the abdomen is shaved and disinfected with alcohol and Betadyne®. A 2.5 cm incision is made from the xyphoid process (Sx) caudally. The intestinal contents are exteriorized onto a wet gauze. The cecum is then manipulated gently for one minute. The abdominal contents are then replaced, the body wall is closed with 4-0 PDS for the fascia muscle layers and wound clips for the skin.

3. Experimental Group 3 (labeled as "Sx+Morphine") is treated similarly to Group #2. When animals recover from the anesthesia, they are treated with subcutaneous injection of morphine sulfate with dose rate of 3 mg of DFNa per 1 kg of body weight.

4. Test Group 4 (labeled as "Sx+IC-2 mg") is treated similarly to Group #2. Prior to closure, sample IC-2.0, which is Interceed® (2×2.5 cm) containing 2 mg diclofenac sodium, is placed on the manipulated cecum.

5. Test Group 5 (labeled as Sx+IC-1.0 mg") is treated similarly to Group #2. Prior to closure, samples IC-1.0, which is Interceed® (2×2.5 cm) containing 1 mg diclofenac sodium, is placed on the manipulated cecum.

6. Test Group 6 (labeled as "Sx+IC-0.3 mg") is treated similarly to Group #2. Prior to closure, samples IC-0.3-A, which is Interceed® (2×2.5 cm) containing 0.3 mg diclofenac sodium, is placed on the manipulated cecum.

7. Test Group 7 (labeled as "Sx+IC-0.1 mg") is treated similarly to Group #2. Prior to closure, sample IC-0.1, which is Interceed® (2×2.5 cm) containing 0.1 mg diclofenac sodium, is placed on the manipulated cecum.

8. Experimental Group 8 (labeled as Sx+IC") is treated similarly to Group #2. Prior to closure, Interceed® (2×2.5 cm) with no drug added, is placed on the manipulated cecum.

9. Test Group 9 (labeled as Sx+Morp+IC-0.3 mg") is treated similarly to Group #3. Prior to closure, samples IC-0.3-B, which is Interceed® (2×2.5 cm) containing 0.3 mg diclofenac sodium, is placed on the manipulated cecum.

10. Test Group 10 (labeled as Sx+Morp+IC-2.0 mg") is treated similarly to Group #3. Prior to closure, samples IC-2.0, which is Interceed® (2×2.5 cm) containing 2.0 mg diclofenac sodium, is placed on the manipulated cecum.

11. Experimental Group 11 (labeled as Sx+0.3 mg DCF") is treated similarly to Group #2. Prior to closure, a slurry of 50 μl saline containing 0.3 mg diclofenac sodium is placed on the manipulated cecum.

All groups are treated with an oral solution of charcoal (10%) in acacia gum (2%) by gavage. Four hours following oral administration, the rats are euthanized with carbon dioxide. The intestines are exteriorized, and the distance traveled by the charcoal meal is measured as well as the full length of the intestines (from the pylorus through the anus). Results are expressed as distance traveled in centimeters as well as percent of distance traveled relative to the full length of the intestines.

Figure 1:
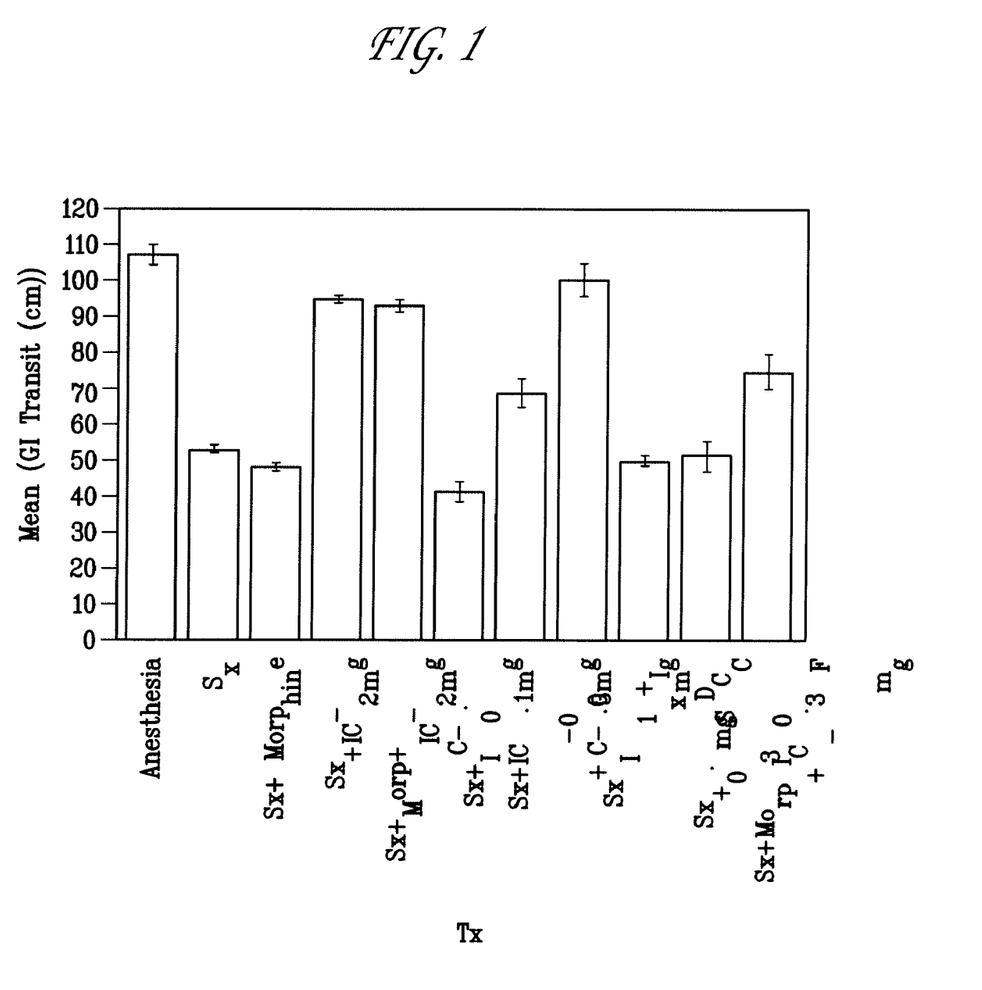
FIG. 1 illustrates the mean gastrointestinal (GI) transit length of a charcoal meal four hours after feeding rats that have ileus induced and treated in accordance with in vivo testing of the ileus prevention compositions and methods herein.
Figure 2:
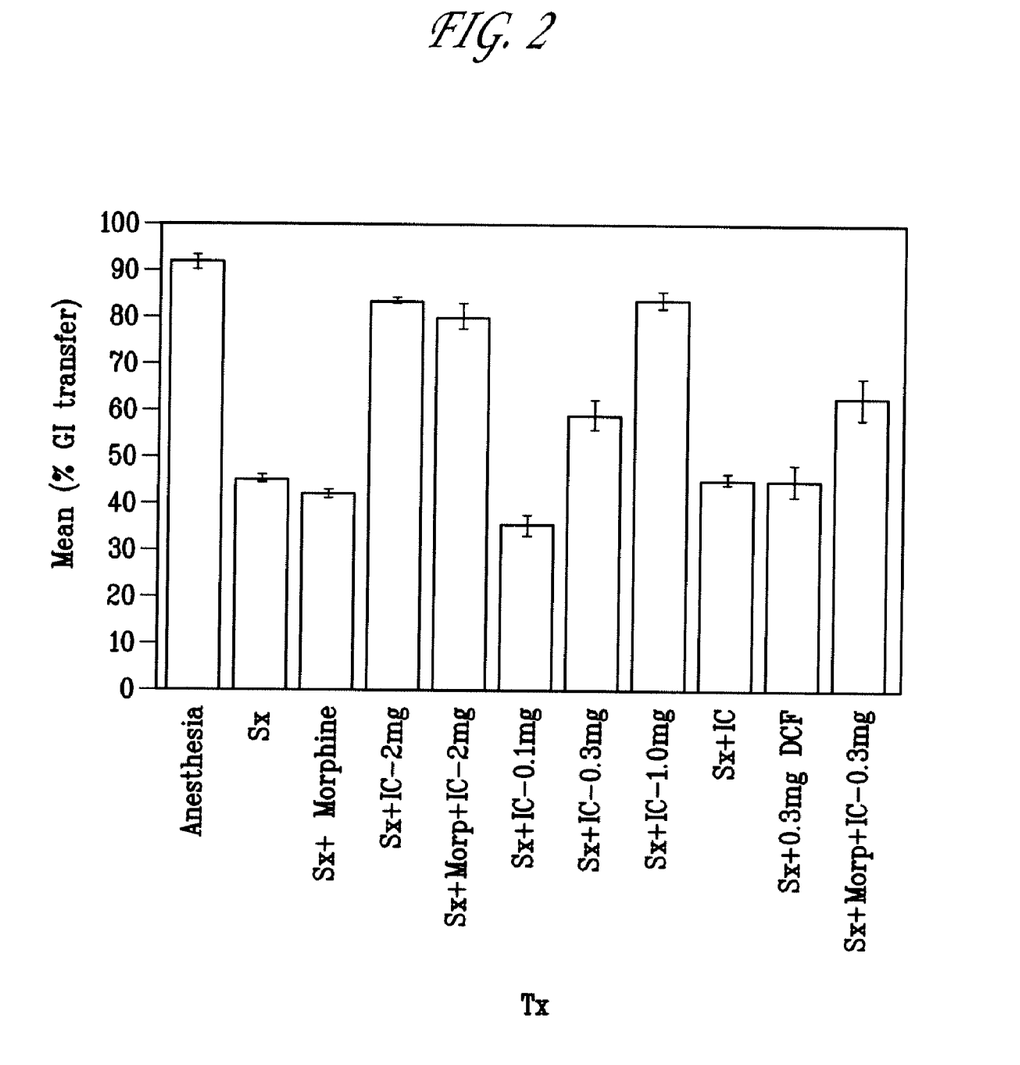
FIG. 2 illustrates the mean percentage of total intestinal length of the GI transit of a charcoal meal four hours after feeding rats that have ileus induced and treated in accordance with in vivo testing of the ileus prevention compositions and methods herein.

The results of this in vivo testing are set forth in FIGS. 1 and 2. As can be seen form both Figures, intestinal transit is markedly decreased by the surgery and is further decreased by the morphine treatment administered after the surgery. Placing Interceed® containing diclofenac, a Cox inhibitor, successfully alleviates this decrease in intestinal transit. A dose response is evident in the effect of diclofenac. A dose of 0.1 mg of diclofenac is not sufficient in this test to alleviate the decrease in intestinal transit, and at a diclofenac dose of 1.0 mg, a maximal effect is achieved. No further enhancement in intestinal transit is observed with sample IC-2.0, the Interceed® sample containing 2 mg diclofenac. (It should be noted that even though diclofenac at a 0.1 mg dose is not sufficient in this test, more potent NSAID Cox inhibitors may very well be effective at doses of 0.1 mg or even lower.)

Neither diclofenac alone nor Interceed® alone are sufficient to produce the observed therapeutic effect. Interceed® containing 0.3 mg diclofenac sodium produces a therapeutic effect (in surgery as well as in surgery and morphine treatment). On the other hand, application of 0.3 mg diclofenac to the cecum, or Interceed® to the cecum, produces no therapeutic effect.

While there has been shown and described what is considered to be preferred embodiments of the invention, it will, of course, be understood that various modifications and changes in composition and method could readily be made without departing from the spirit of the invention. It is therefore intended that the invention be not limited to the exact compositions and methods described and illustrated, but should be construed as cover all modifications that may fall within the scope of the appended claims.

What is claimed is:

1. A composition for application to intestinal and other visceral serosal surfaces to thereby reduce postoperative ileus and gastric stasis, which composition comprises oxidized regenerated cellulose and a non-steroidal anti-inflammatory drug or derivatives thereof selected from the group consisting of alkali metal salts thereof, esters thereof, and isomers thereof, wherein said non-steroidal anti-inflammatory drug is a Cox inhibitor.

2. A composition according to claim 1 wherein said non-steroidal anti-inflammatory drug is a Cox inhibitor selected from the group consisting of propionic acid derivatives; acetic acid derivatives; fenamic acid derivatives; biphenylcarboxylic acid derivatives; oxicams; and Cox2 inhibitors.

3. A composition according to claim 1 wherein the non-steroidal anti-inflammatory drug is selected from the group consisting of diclofenac or mefenamic acid, or an alkali metal salt thereof.

4. A composition according to claim 1 wherein the non-steroidal anti-inflammatory drug is diclofenac or an alkali metal salt thereof.

5. A composition according to claim 1 wherein the weight ratio of the Cox inhibitor to the oxidized regenerated cellulose within the composition ranges from about 1:1000 to about 1:35.

6. A composition according to claim 5 wherein the concentration of the non-steroidal anti-inflammatory drug ranges from about 0.01% to about 10% by weight of the composition.

7. A composition according to claim 1 wherein the composition is in a form selected from the group consisting of a textile, a blend of particles, a foam sponge, foam beads, and agglomerates.

8. A composition according to claim 7 which comprises an oxidized regenerated cellulose textile or particles and said non-steroidal anti-inflammatory drug wherein the non-steroidal anti-inflammatory drug is incorporated into the composition by (a) dip coating the oxidized regenerated cellulose textile in a solution or suspension of the non-steroidal anti-inflammatory drug; (b) spray coating a solution or suspension of the non-steroidal anti-inflammatory drug onto the oxidized regenerated cellulose textile; (c) laminating at least one polymer film formed from a solution or suspension of the non-steroidal anti-inflammatory drug onto the oxidized regenerated cellulose textile; or (d) forming a microporous polymeric matrix with the non-steroidal anti-inflammatory drug, and the oxidized regenerated cellulose textile or particles.

9. A composition according to claim 8 wherein the polymer film used in any laminating step comprises a polymer selected from the group consisting of poly(acrylic acid), hydroxylpropyl methyl cellulose, polyvinyl pyrrolidone, polyethylene glycol, and polyethylene oxide.

10. A composition according to claim 8 wherein the non-steroidal anti-inflammatory drug is formed into a microporous polymeric matrix using a binder comprising at least one polysaccharide selected from the group consisting of cellulose, alkyl cellulose, alkylhydroxyalkyl cellulose, hydroxyalkyl cellulose, cellulose sulfate, salts of carboxymethyl cellulose, carboxymethyl cellulose, carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylase, amylopectin, poly-N-glucosamine, polymannuronic acid, polyglucuronic acid polyguluronic acid and derivatives thereof.

11. A composition according to claim 7 in the form of a particle blend wherein the particles comprise oxidized regenerated cellulose particles having an average particle size of 1 to 1000 microns, and non-steroidal anti-inflammatory drug particles.

12. A composition according to claim 11 wherein the oxidized regenerated cellulose particles have an average size of 20 to 25 microns.

13. A composition according to claim 1 wherein the composition further comprises an additional component selected from the group consisting of stabilizers, wetting agents, preservatives, antibiotics, antiviral agents, anti-fungal agents, anti-microbial agents, and mixtures of these additional components.

14. A method of reducing postoperative ileus and gastric stasis, which method comprises administering directly to the serosal surfaces of the gastrointestinal and other visceral organs of a surgical patient an effective amount of a composition which comprises an oxidized regenerated cellulose component and a non-steroidal anti-inflammatory drug or derivatives thereof selected from the group consisting of alkali metal salts thereof, esters thereof, and isomers thereof, which functions as a cyclooxygenase enzyme inhibitor.

15. A method according to claim 14 wherein the non-steroidal anti-inflammatory drug component of the administered composition is a Cox inhibitor selected from the group consisting of propionic acid derivatives; acetic acid derivatives; fenamic acid derivatives; biphenylcarboxylic acid derivatives; oxicams; and Cox2 inhibitors.

16. A method according to claim 14 wherein the non-steroidal anti-inflammatory drug is selected from the group consisting of diclofenac or mefenamic acid or an alkali metal salt thereof.

17. A method according to claim 14 wherein within the administered composition the weight ratio of the Cox inhibitor to the oxidized regenerated cellulose ranges from about 1:1000 to about 1:35.

18. A method according to claim 14 wherein within the administered composition the concentration of the non-steroidal anti-inflammatory drug ranges from about 0.01% to about 10% by weight of the composition.

19. A method according to claim 14 wherein the administered composition is in a form selected from the group consisting of a textile, a blend of particles, a foam sponge, foam beads, and agglomerates.

20. A method according to claim 19 wherein the administered composition comprises an oxidized regenerated cellulose textile or particles and said non-steroidal anti-inflammatory drug wherein the non-steroidal anti-inflammatory drug is incorporated into the composition by (a) dip coating the oxidized regenerated cellulose textile in a solution or suspension of the non-steroidal anti-inflammatory drug; (b) spray coating a solution or suspension of the non-steroidal anti-inflammatory drug onto the oxidized regenerated cellulose textile; (c) laminating at least one polymer film formed from a solution or suspension of the non-steroidal anti-inflammatory drug onto the oxidized regenerated cellulose textile; or (d) forming a microporous polymeric matrix with the non-steroidal anti-inflammatory drug, and the oxidized regenerated cellulose powders or textile.

21. A method according to claim 20 wherein the polymer film used in any laminating step comprises a polymer selected from the group consisting of poly(acrylic acid), hydroxylpropyl methyl cellulose, polyvinyl pyrrolidone, polyethylene glycol, and polyethylene oxide.

22. A method according to claim 20 wherein the non-steroidal anti-inflammatory drug is formed into a microporous polymeric matrix using a binder comprising at least one polysaccharide selected from the group consisting of cellulose, alkyl cellulose, alkylhydroxyalkyl cellulose, hydroxyalkyl cellulose, cellulose sulfate, salts of carboxymethyl cellulose, carboxymethyl cellulose, carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylase, amylopectin, poly-N-glucosamine, polymannuronic acid, polyglucuronic acid polyguluronic acid and derivatives thereof.

23. A method according to claim 19 wherein the administered composition is in the form of a particle blend wherein the particles comprise oxidized regenerated cellulose particles having an average particle size of 1 to 1000 microns, and non-steroidal anti-inflammatory drug particles.

24. A method according to claim 23 wherein the oxidized regenerated cellulose particles have an average size of 20 to 25 microns.

25. A method according to claim 19 wherein the administered composition further comprises an additional component selected from the group consisting of stabilizers, wetting agents, preservatives, antibiotics, antiviral agents, anti-fungal agents, anti-microbial agents, and mixtures of these additional components.

* * * * *